United States Patent [19]
Davis et al.

[11] Patent Number: 6,133,429
[45] Date of Patent: Oct. 17, 2000

[54] CHROMOPHORES USEFUL FOR THE PREPARATION OF NOVEL TANDEM CONJUGATES

[75] Inventors: Kenneth A. Davis, Woodside; James E. Bishop, Santa Cruz; Barnaby Abrams, San Carlos, all of Calif.

[73] Assignee: Becton Dickinson and Company, Franklin Lakes, N.J.

[21] Appl. No.: 08/943,491

[22] Filed: Oct. 3, 1997

[51] Int. Cl.[7] .......................... G01N 33/533; C07K 16/44
[52] U.S. Cl. ...................... 530/391.5; 436/501; 436/800; 530/391.3; 530/402; 530/403; 435/40.5
[58] Field of Search .............................. 530/391.5, 391.3, 530/402, 403; 436/546, 800; 435/40.5

[56] References Cited

U.S. PATENT DOCUMENTS

| | | | |
|---|---|---|---|
| 4,520,110 | 5/1985 | Stryer et al. | 436/501 |
| 4,542,104 | 9/1985 | Stryer et al. | 436/536 |
| 4,876,190 | 10/1989 | Recktenwald | 435/7 |
| 4,981,977 | 1/1991 | Southwick et al. | 548/455 |
| 5,145,772 | 9/1992 | Voyta et al. | 435/4 |
| 5,171,846 | 12/1992 | Gupta | 530/400 |
| 5,597,696 | 1/1997 | Linn et al. | 435/6 |
| 5,622,821 | 4/1997 | Selvin et al. | 435/6 |
| 5,714,386 | 2/1998 | Roederer | 436/546 |

FOREIGN PATENT DOCUMENTS

| | | | |
|---|---|---|---|
| 0 314 406 B1 | 8/1993 | European Pat. Off. | G01N 33/533 |
| 0 747 700 | 12/1996 | European Pat. Off. | G01N 33/533 |
| 0 800 083 A2 | 4/1997 | European Pat. Off. | G01N 33/532 |

OTHER PUBLICATIONS

R. Robins, Methods Mol. Biol. (Totowa, N.J.), 80 (Immunochemical Protocols 2nd edition), 337–346 (1998).
F. Laso et al, Cytometry (Dec. 15, 1996), 26 (4), 275–280.
Kuase et al, Blood 87: (1), 1, Jan. 1996.
Ballou, et al., "Tumor labeling in vivo using cyanine–conjugated monoclonal antibodies" *Cancer Immunol Immunother* 41:257–263 (1995).
Beavis and Pennline, "ALLO–7: A New Fluorescent Tandem Dye for Use in Flow Cytometry" *Cytometry* 24:390–394 (1996).
Chen and Evangelista, "Feasibility Studies for Simultaneous Immunochemical Multianalyte Drug Assay by Capillary Electrophoresis with Laser–Induced Fluorescence" *Clin. Chem.* 40(9):1819–1822 (1994).
Daubner, et al., "Yellow light emission of *Vibrio fischeri* strain Y—1: Purification and characterization of the energy–accepting yellow fluorescent protein" *Proc. Natl. Acad. Sci. USA* 84:8912–8916 (1987).
Ernst, et al., "Cyanine Dye Labeling Reagents for Sulhydryl Groups[1]" *Cytometry* 10:3–10 (1989).
Feeney, R. E., "Chemical modification of proteins: comments and perspectives" *Int. J. Peptide Protein Res.* 29:145–161 (1987).
Glazer and Stryer, "Fluorescent Tandem Phycobiliprotein Conjugates" *Biophys J.* 43:383–386 (1983).
Han et al., "Chemical Cross–Links of Proteins By Using Bifunctional Reagents" *Int. J. Biochem* 16(2):129–145 (1984).

Hung, et al., "Cyanine Dyes with High Absorption Cross Section as Donor Chromophores in Energy Transfer Primers[1]" *Analytical Biochemistry* 243:15–27 (1996).
Mujumdar, et al., "Cyanine–Labeling Reagents: Sulfobenzindocyanine Succinimidyl Esters" *Bioconjugate Chem.* 7:356–362 (1996).
Mujumdar, et al., "Cyanine Dye Labeling Reagents Containing Isothiocyanate Groups[1]" *Cytometry* 10:11–19 (1989).
Mujumdar, et al., "Cyanine Dye Labeling Reagents: Sulfoindocyanine Succinimidyl Esters" *Bioconjugate Chemistry* 4(2):105–111 (1993).
Prasher, et al., "Primary structure of the *Aequorea victoria* green–fluorescent protein" *Gene* 111:229–233 (1992).
Rye, et al., "Stable fluorescent complexes of double–stranded DNA with bis–intercalating asymmetric cyanine dyes: properties and applications" *Nucleic Acids Research* 20(11):2803–2812 (1992).
Shapiro, M.D., H.M., "Cyanine Dye Labels: From Cy–Fi to Hi5 for Cy5" *Practical Flow Cytometry, Third Edition* 281–282 (1995).
Southwick, et al., "Cyanine Dye Labeling Reagents–Carboxymethylindocyanine Succinimidyl Esters[1]" *Cytometry* : 418–430 (1990).
van Vugt, et al., "Binding of PE–CY5 Conjugates to the Human High–Affinity Receptor for IgG (CD64)" *Blood* 88:2358–2359 (1996).
Waggoner, et al., "PE–CY5 A New Fluoprescent Antibody Label for Three–Color Flow Cytometry with a Single Laser" *Ann. N.Y. Acad. Sci.* 677:185–193 (1993).
Yu, et al., "Cyanine dye dUTP analogs for enzymatic labeling of DNA probes" *Nucleic Acids Research* 22(15):3226–3232 (1994).
Zalipsky, S., "Functionalized Poly(ethylene glycol) for Preparation of Biologically Relevant Conjugates" *Bioconjugate Chem.* 6:150–165 (1995).
Zeng, et al., "Fluorescence Energy–Transfer Cyanine Heteroodimers with High Affinity for Double–Stranded DNA" *Analytical Biochemistry* 231(1):256–260 (1995).
Zhu, et al., "Directly labeled DNA probes using fluorescent nucleotides with different length linkers" *Nucleic Acids Research* 22(16):3418–3422 (1994).

*Primary Examiner*—Mary E. Ceperley
*Attorney, Agent, or Firm*—Daniel M. Becker; Vicki S. Veenker; Fish & Neave

[57] ABSTRACT

The inventors herein disclose new heterobifunctional chromophores that are capable of coupling with two distinct moieties. One moiety may be either a signal-enhancing agent or a blocking agent. The second moiety may be one member of a specific binding pair. The invention is based in part on the surprising result that when a chromophore is used as a "cross-linker" between a signal-enhancing agent and a member of a binding pair (essentially being buried between the two), the signal of the chromophore is not quenched. This arrangement, wherein the chromophore acts simultaneously as a cross-linker and a detectable compound, provides significant advantages over previously known compounds since the chromophore is sterically hindered from interacting non-specifically with substances present in the test systems. Moreover, the chromophore can be used as a cross-linker with little or no loss of detectable signal.

71 Claims, 4 Drawing Sheets

CD3-Cy5.5-PerCP

CD3-PerCP-Cy5.5

CD3-PerCP

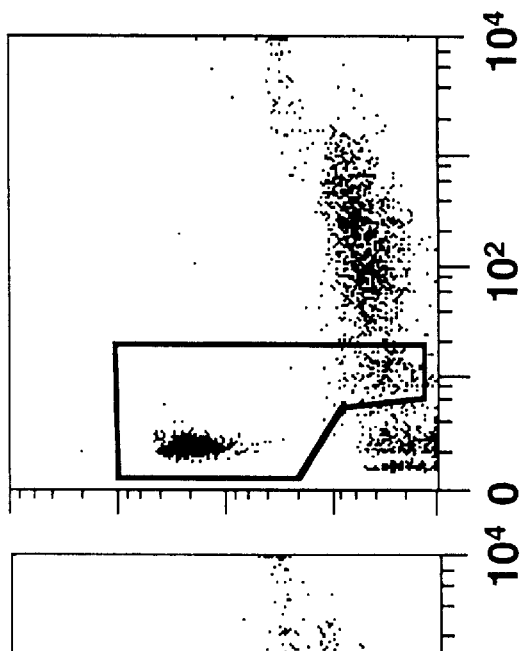
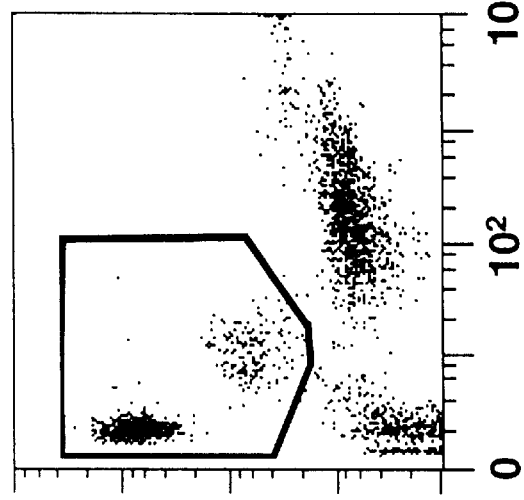
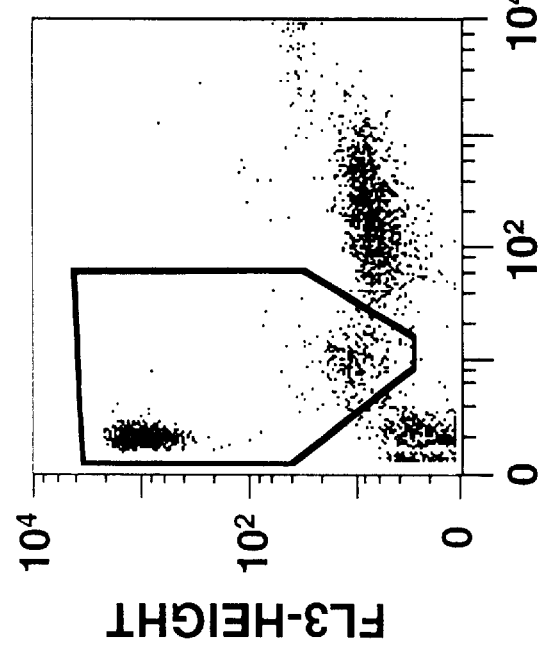

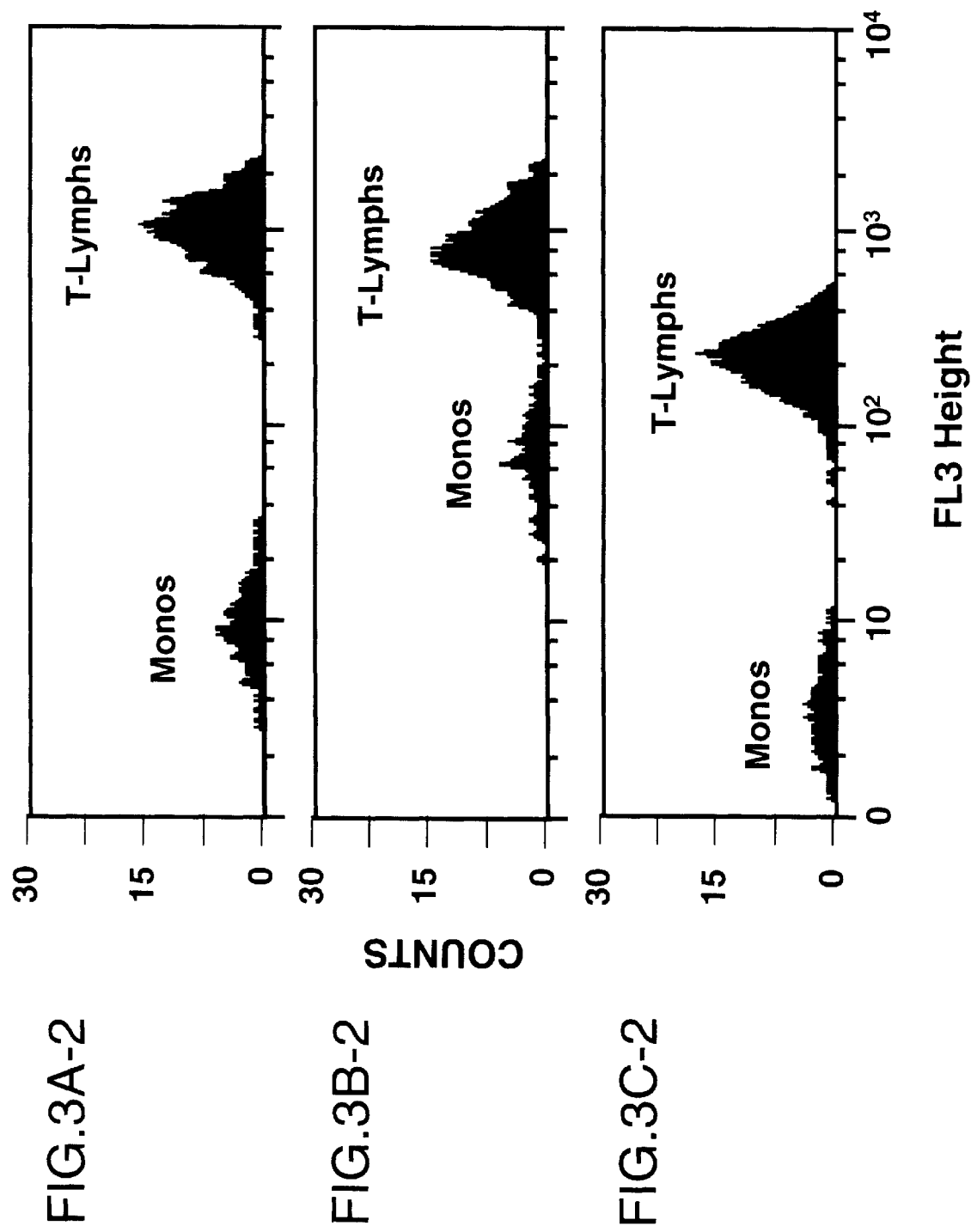

CHROMOPHORES USEFUL FOR THE PREPARATION OF NOVEL TANDEM CONJUGATES

FIELD OF THE INVENTION

The present invention relates to novel heterobifunctional chromophores useful for labeling materials such as proteins or cells, complexes containing the heterobifunctional chromophores, and methods of using them.

BACKGROUND OF THE INVENTION

Fluorescent labeling reagents have become increasingly useful investigative tools. The wider use of fluorescently labeled probes has resulted partly from advances in instrumentation and partly from the availability of new and improved fluorescent dyes. The cyanine dyes have received particular interest since relatively minor alterations in their chemical structure allows for variation in their excitation and emission wavelengths, an advantage for designing multicolor systems useful for simultaneous detection of more than one fluorescent probe.

More recently the cyanine dyes have become widely used as one component of a tandem conjugate with a second fluor, often proteinaceous fluorophores such as phycoerythrin (PE) or Peridinin-chlorophyll a-protein (PerCP). When the emission spectrum of one fluor overlaps the excitation spectrum of another, and they are sufficiently close to each other (<10 nm), it is possible for the excitation energy of the first fluor to be transferred to the second through a fluorescent resonance energy transfer process (Glazer and Stryer, Biophys J. 43:383–386, 1983).

A significant drawback to the use of these reagents, particularly for labeling antibodies used in analysis and sorting of blood cells, is the tendency for the fluor complex to bind to components of the system in an indiscriminate manner (van Vugt, et al, Blood 88:2358–2359, 1996; Beavis and Pennline, Cytometry 24:390–394, 1996; Shapiro, Practical Flow Cytometry, 3rd ed, pg 282, 1995).

A need, therefore, still exists for new labeling reagents that are sensitive, easily detected, and exhibit little or no undesirable fluor-mediated binding.

BRIEF DESCRIPTION OF THE INVENTION

The inventors herein disclose new heterobifunctional chromophores that are capable of coupling with two distinct moieties. One moiety may be either a signal-enhancing agent or a blocking agent. The second moiety may be one member of a specific binding pair. The invention is based in part on the surprising result that when a chromophore is used as a "cross-linker" between a signal-enhancing agent and a member of a binding pair (essentially being buried between the two), the signal of the chromophore is not quenched. This arrangement, wherein the chromophore acts simultaneously as a cross-linker and a detectable compound, provides significant advantages over previously known compounds since the chromophore is sterically hindered from interacting non-specifically with substances present in the analytical system. Moreover, the chromophore can be used as a cross-linker with little or no loss of detectable signal.

Also disclosed are complexes formed between a heterobifunctional chromophore and a signal-enhancing agent. The signal-enhancing agent is capable of participating in resonance energy transfer reactions. The interaction between the chromophore and the signal-enhancing agent may be covalent or non-covalent. Alternatively, the heterobifunctional chromophore may form a complex with a blocking agent.

Also disclosed are methods of making the heterobifunctional chromophores of the invention and methods for making complexes having the heterobifunctional chromophores as one of their components. The complexes are suitable for a variety of uses such as the labeling of antibodies for use as immunologic reagents and the labeling of DNA for use as a probe. Tandem complexes available in the art do not employ heterobifunctional chromophores (Waggnoner, et al, EP 747 700, published Dec. 11, 1996; Stryer, et al, U.S. Pat. No. 4,542,105, issued Sep. 17, 1985).

By "heterobifunctional" it is meant that the chromophore has two different functional groups, each of which is capable of forming a linkage with a second molecule. Suitable examples of functional groups include succinimidyl esters, isothiocyanates, carbodiimide activated carboxyls, hydrazide activated aldehyde imidoesters, maleimides (hereinafter "Mal"), vinyl sulfones, active halogens, pyridyldisulfides, thiols, and the like.

BRIEF DESCRIPTION OF THE DRAWINGS

FIG. 3 compares the fluor-specific binding to monocytes of CD3-PerCP, CD3-PerCP-Cy5.5 (Cy5.5 "exposed") and CD3-Cy5.5-PerCP (Cy5.5 "buried") (See Example 2). The dot plots of side scatter vs F13 (A-1, B-1 and C-1) show gating of T-lymphocytes and monocytes, which are displayed as an FL3 histogram of PerCP/PerCP-Cy5.5 intensity (A-2, B-2 and C-2). CD3 antibody labeled with Mal/Cy5.5-PerCP complex of the invention shows little or no fluor-specific binding to monocytes.

DETAILED DESCRIPTION OF THE INVENTION

Figure 1:
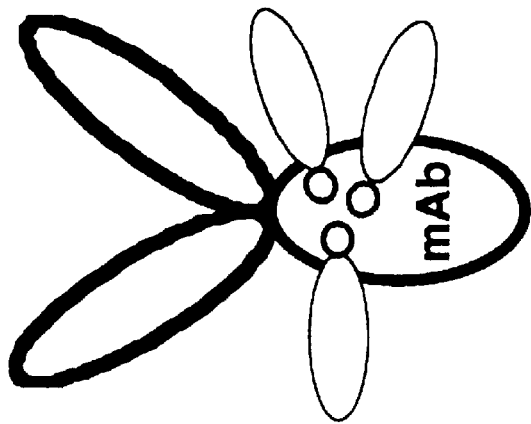
FIG. 1 schematically illustrates the manner in which the conjugates of the invention interact with one component of a binding pair, in this illustration, an antibody. Previously, dye conjugates were bound to the antibody via a cross-linking moiety on the signal-enhancing agent leaving the chromophore exposed to its surroundings so that it could interact with vessel walls, cell surfaces, etc. In the conjugates of the invention, the chromophore is heterobifunctionalized so that it functions both as a detectable dye compound and a crosslinking moiety attaching the chromophore:signal-enhancer complex to the antibody (effectively "burying" the chromophore and blocking its ability to bind non-specifically).
Figure 1:
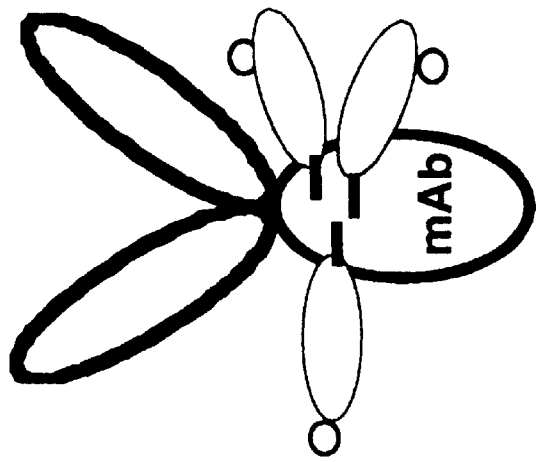

The invention herein discloses heterobifunctionalized chromophores, wherein one functionality on said chromophore is capable of coupling with a signal-enhancing agent or a blocking agent, and the other functionality is capable of coupling with a member of a specific binding pair. These conjugates can be used in assays involving non-covalent binding to the complementary member of the specific binding pair. Thus, the present invention should find widespread application since a wide variety of methods involve competitive or non-competitive binding of one member of a binding pair to another for detection, analysis or measurement of the presence of the complementary member of the binding pair.

Similar chromophore complexes known in the art have been widely used but exhibit significant drawbacks including relative dimness (making them unsuitable for detection of complementary binding pair members present at low levels), bleaching, signal spillover into neighboring detection channels (a critical problem when detecting multiple colors simultaneously), instability, and nonspecific binding to irrelevant or inappropriate components of the analytical system. The chromophore and methods of the invention, however, overcome these problems, particularly the problem of non-specific binding.

By "chromophore" it is meant a compound capable of being detected calorimetrically or fluorometrically. The specific examples disclosed herein describe chromophores detected by fluorescence. It should be understood, however, that the compounds and methods described can equally be utilized with chromophores that are detected by other means readily available to one skilled in the art, such as, for example absorbance or phosphorescence.

Suitable chromophores are detectable compounds having two functional groups, each of which is capable of undergoing a chemical reaction with a second compound such that the chromophore and second compound form a chemical interaction. The chromophore may be a fluorescent dye, a non-fluorescent dye, or the like. Examples of suitable chromophores include, but are not limited to, fluorescein and its derivatives and the cyanine dyes such as isothiocyanines, merocyanines, indodicarbocyanines (ex. Cy3, Cy3.5, Cy5, Cy5.5), indotricarbocyanines (ex. Cy7, Cy7.5), thiazole orange, oxazole yellow, and CYA (3-(epsilon-carboxypentyl)-3'ethyl-5,5'dimethyloxacarbocyanine), and the like, (see Mujumdar, et al Bioconjugate Chem. 4(2):105–111, 1993; Ernst, et al, Cytometry 10:3–10, 1989; Mujumdar, et al, Cytometry 10:1119, 1989; Southwick, et al, Cytometry 11:418–430, 1990; Hung, et al, Anal. Biochem. 243(1): 15–27, 1996; Nucleic Acids Res. 20(11):2803–2812, 1992; Mujumdar, et al, Bioconjugate Chem. 7:356–362, 1996; Southwick and Waggoner, U.S. Pat. No. 4,981,977, issued Jan. 1, 1991).

Particularly preferred cyanine dyes are the indodicarbocyanines and the indotricarbocyanines. Synthesis of these dyes is described in detail in Mujumdar, et al, Bioconjugate Chem. 7:356–362, 1996 and Southwick, et al, Cytometry 11:418–430, 1990. A particularly preferred chromophore is Cy5.5-Bis-OSu (compound X (Cy5.205.OSu) in Mujumdar, 1996, supra). This dye contains two succinimidyl ester reactive groups which can be readily derivatized as described below. It is understood by those skilled in the art that a heterobifunctional chromophore of the invention can be isolated or synthesized such that it contains two identical reactive groups, one of which can be subsequently modified to create heterofunctionality. Alternatively the heterobifunctional chromophore can be initially synthesized with different reactive groups.

The chromophores of the invention can be coupled to either a signal-enhancing agent or a blocking agent. By "signal-enhancing agent" it is meant a compound that is capable of forming a complex with the heterobifunctional chromophore and is additionally capable of emitting a detectable signal, for example, a fluorescent signal.

A suitable signal-enhancing agent, in the case of fluorescing compounds, will be capable of participating in fluorescent resonance energy transfer (FRET) reactions, (see, Glazer and Stryer, Biophys. J. 43:383–386, 1983). In FRET reactions, a donor molecule becomes excited at a wavelength A and emits radiation at a wavelength B. An acceptor molecule is subsequently excited by the radiation emitted from the donor molecule (wavelength B) and emits at a wavelength C. A fluorescent signal-enhancing molecule useful in the invention can act as either donor molecule or acceptor molecule.

Examples of signal-enhancing agents include, but are not limited to, small organic molecules such as fluorescein and its derivatives, Texas red, rhodamine, umbelliferone, lanthanide chelates, dipyrometheneboron difloride, and Rhodol green, and proteinaceous fluorophores such as the phycobiliproteins (phycoerythrin (PE), allophycocyanin (APC)), Peridinin-chlorophyll-proteins (PerCP), yellow fluorescent proteins (YFPs), green fluorescent proteins (GFPs), and the like, (see Daubner, et al, PNAS 84(24):8912–8916, 1987; Prasher, et al, Gene 111(2):229–233, 1992; Recktenwald, U.S. Pat. No. 4,876,190, issued Oct. 24, 1989, and publications cited therein; Stryer, et al, U.S. Pat. No. 4,520,110, issued May 28, 1985; Selvin, et al, U.S. Pat. No. 5,622,821, issued Apr. 22, 1997).

A particularly preferred signal-enhancing agent is PerCP, which can be isolated from a variety of phytoplankton species. This proteinaceous fluorophore contains a wide range of functional groups for conjugation including amino, and carboxyl groups. PerCP and its isolation is described in detail in Recktenwald, U.S. Pat. No. 4,876,190, issued Oct. 24, 1989, incorporated by reference herein in its entirety. While PerCP itself has some utility as a fluorescent dye, its lack of sensitivity (relative dimness) and its tendency to rapidly bleach when used with a strong laser limit its applicability. The invention complexes are significantly brighter that PerCP alone. For example, the heterobifunctional chromophore-PerCP complex used in the Examples below is approximately five times as bright as PerCP used alone. In addition, this complex does not photobleach, allowing the complex to be useful in stream-in-air flow cytometers and fluorescent cells sorters, which generally use stronger lasers.

The chromophores of the invention may alternatively be coupled to a blocking agent. By "blocking agent" it is meant a compound that is capable of forming a complex with the heterobifunctional chromophore but which is generally unreactive with other substances once the complex is formed. A preferred blocking agent will be capable of reducing the ability of the chromophore to participate in chromophore-mediated undesirable binding. The interaction between the chromophore and the blocking agent may be covalent or non-covalent. A signal-enhancing agent may also be a blocking agent.

Suitable blocking agents are relatively large molecules that are relatively inert. Well known examples of blocking agents used in the art include, but are not limited to, serum proteins such as serum albumins (such as bovine serum albumin) and alpha and gamma globulins; milk proteins such as casein and cellulose. Particularly preferred blocking agents are the polyalkylene oxides (or polyethylene glycols (PEGs)).

PEGs are polyether diols of the general structure HO—$(CH_2CH_2O)_n$—$CH_2CH_2$—OH. Their desirability as a blocking agent derives from, among other things, their wide range of solubilities in both aqueous and organic media, their relative lack of toxicity and immunogenicity, their nonbiodegradability and their relative inertness once derivatized. They are commercially available in a variety of molecular weights, typically between 1000 and 20,000 Daltons. One of skill in the art would easily be able to select the appropriate size of PEG molecule for use as a blocking agent with the chromophores employed in accordance with the present invention. Monomethyl PEG (mPEG) is often used to prepare conjugates since the presence of only one derivatizable end group on mPEG minimizes crosslinking and improves the homogeneity of PEG-conjugate preparations. A review of functionalized PEGs for the preparation of conjugates can be found in Zalipsky, Bioconjugate Chem. 6:150–165, 1995.

The chromophore of the invention is additionally able to couple with a member of a specific binding pair. By "specific binding pair" it is meant a pair of molecules that specifically interact with one another in preference to interaction with any other molecule. The specificity of binding between two molecules can also be judged by the strength of their interaction with one another. Binding pairs are said to exhibit specific binding when they exhibit avidity of at least $10^7$, preferably at least $10^8$, more preferably at least $10^9$ liters/mole. One example of a specific binding pair is an antibody and antigen.

A member of a binding pair suitable for conjugation with a chromophore complex of the invention will comprise at least one, functional group(s) capable of coupling to a functional group of the heterobifunctionalized chromophore with up to 10 or higher being possible. Examples of functional groups include amino, thio, carboxyl, and the like. Binding pairs can include, for example without limitation, antibodies and antigens or haptens, nucleotides (which specifically bind to other oligonucleotides when oligomerized), biotin and avidin or streptavidin, ligands and receptors, and the like. The chromophore complex may be coupled to either member of the binding pair as would be appropriate for the intended use of the labeled conjugate.

The chromophores of the invention can couple with a signal-enhancing agent or blocking reagent and member of a binding pair by covalent or non-covalent means. Non-covalent means include electrostatic means, hydrogen bonding, and the like.

Depending on the molecules employed for the preparation of conjugated complexes according to the invention, a wide variety of linking groups may be used for coupling by covalent interactions, both for linking the chromophore to the signal-enhancing agent or blocking agent and linking the chromophore to the member of the binding pair. Suitable functional groups for the heterobifunctionalized chromophore include, but are not limited to, succinimidyl, isothiocyanate, carbodiimide activated carboxyl, hydrazide activated aldehyde imidoester, and the like, all of which react with amino groups; and maleimide, vinyl sulfone, active halogen, pyridyldisulfide, and the like, all of which react with sulfhydryl; and so on. General discussions of covalent cross-linking using reagents having different functional groups can be found in Han et al, Int. J. Biochem 16(2):129–145, 1984 and Feeney, Int. J. Peptide Protein Res. 29:145–161, 1987. Methods of attaching chromophores to oligonucleotides via a linking spacer can be found in Linn, et al, U.S. Pat. No. 5,597,696, issued Jan. 28, 1997, incorporated by reference herein in its entirety.

The utility of the chromophores and complexes of the invention is readily recognized by those skilled in the art. The chromophore complexes can be used to label antibodies (polyclonal or monoclonal) which are then useful in a variety of methodologies including fluorescent activated cell sorting or analysis, immunoassays, immunostaining, and the like. Antibody conjugates can also be used for diagnostic purposes, both in vitro and in vivo. Ballou, et al, for example, describe a method of using antibody conjugates for the detection of tumors in vivo. (Ballou, et al, Cancer Immunol. Immunother. 41(4):257–263, 1995) Lanza, et al, describe an in vitro method of diagnosing leukemia using antibody conjugates. (Lanza, et al, Leuk Lymphoma 18 (Supp 1):25–30, 1995)

Non-antibody proteins can also be labeled with the chromophore complexes disclosed herein. For example, antigens may be coupled with a chromophore complex and used in competitive immunoassays. Protein ligands such as growth factors or cytokines can be labeled with chromophore complexes and subsequently used to study ligand:receptor interactions for either research or clinical purposes.

The complexes of the invention can be used to label a variety of non-protein molecules. Chen and Evangelista, for example, describe a multianalyte drug assay wherein labeled morphine and phencyclidine (PCP) are used in a competitive immunoassay to detect drug levels in urine (Chen and Evangelista, Clin. Chem. 40(9):1819–1822, 1994).

Nucleotides or oligonucleotides can be labeled using the chromophore complexes disclosed herein. Individual nucleotide conjugates can be subsequently incorporated into oligonucleotides by nick translation or polymerase chain reaction (PCR) (Zhu, et al, Nucleic Acids Res. 22(16) :3418–3422, 1994). Alternatively, oligonucleotides can be directly conjugated with the chromophore complexes (Zheng, et al, Anal. Biochem 231(1):256–260, 1995). The resulting labeled oligonucleotides (by either method) are useful in both research and clinical applications including DNA and RNA hybridization-based diagnostic methods, DNA and RNA sequencing, restriction fragment mapping, fluorescence in situ hybridization (FISH), and the like, (see, for example, Zeng, et al, supra; Yu, et al, Nucleic Acids Res. 22(15):3226–3232, 1994; Hung, et al, Anal Biochem 243 (1):15–27, 1996).

The complexes of the invention can be included as reagents in kits (either as starting materials (heterobifunctionalized chromophore and signal-enhancing agent) or pre-formed complexes) provided for use in, for example, the methodologies described above.

The invention is described in greater detail by reference to the following non-limiting examples.

EXAMPLE 1

Synthesis of Cy5.5-PerCP

Twelve volumes of the chromophore Cy5.5-Bis-OSu Reactive Dye (OSu/Cy5.5/OSu) (Amersham Life Science, Cat. No. R15500: 33 mM in dimethyl formamide (DMF)), were added to 8 volumes of DMF, 76 volumes of buffer (20 mM morpholinoethane sulfonic acid (MES), 1 mM ethylene diamine tetraacetic acid (EDTA), pH 7.0), and 4 volumes of 100 mM mercaptoethylamine-HCl (Aldrich Cat. No. 12,292-0). After a 20 minute incubation at room temperature, 9 volumes of 500 mM bis-maleimidotriethylene glycol (Molecular BioSciences Cat. No. 46777) in DMF were added and incubation continued a further 20 minutes at room temperature. The reaction mixture containing the heterobifunctional Cy5.5 (Mal/Cy5.5/OSu) and other reaction products was stored on ice if to be used immediately or at −80° C. for longer term storage.

PerCP, 50 nmoles (1.8 mg, QuantaPhy, Inc.) in 50 mM Na phosphate, 1 mM EDTA pH 8.0 was incubated with 100 nmoles of Mal/Cy5.5/OSu for 30 minutes at room temperature. These conditions were selected to minimize the number of PerCP molecules containing two chromophore molecules. The amino groups of PerCP react with the remaining succinimidyl ester moiety (OSu) of the Mal/Cy5.5/OSu. The Mal/Cy5.5-PerCP complex was separated from free Mal/

Cy5.5/OSu and other reaction products by buffer exchange into a buffer containing 0.14 M Na acetate (pH 5.5) and 1 mM EDTA using Sephadex™ G-50. The ratio of Cy5.5 to PerCP was determined by absorption at 280, 478 and 674 nm and found to be 0.6:1.

An antibody specific to T-lymphocytes (CD3(Leu4) Becton Dickinson Immunocytometry Systems) was labeled with Mal/Cy5.5-PerCP by standard means. Briefly, the antibody was derivatized so as to have 6–10 free sulfhydryl moieties per antibody molecule. The reduced antibody was then incubated with a 10 fold excess of Mal/Cy5.5-PerCP, then fractionated by gel filtration on a column containing Superose™ 6. The fractions containing antibody conjugated to "buried" Cy5.5-PerCP (CD3-Cy5.5-PerCP) were pooled and used for further studies.

Antibody labeled with the "exposed" Cy5.5 complex of the prior art was synthesized for comparison with the "buried" Cy5.5 complex of the invention. PerCP was derivatized with maleimide groups using succinimidyl 4-(N-maleimidomethyl)-cyclohexane-1-carboxylate (SMCC, Pierce Biochemical Corp.) to from PerCP/Mal. PerCP/Mal was then coupled to Cy5.5-mono-OSu (Amersham Life-Science Cat. No. R15600) to form Mal/PerCP-Cy5.5. This complex was used to label CD3 antibody as described above. The resulting labeled antibody conjugate (CD3-PerCP-Cy5.5) leaves the cyanine dye exposed.

EXAMPLE 2

Staining of Whole Blood with CD3-Cy5.5-PerCP

Normal human blood (50 μl) containing EDTA was incubated with 38 ng (10 μl) CD3-Cy5.5-PerCP (Cy5.5 buried), CD3-PerCP-Cy5.5 (Cy5.5 exposed), or CD3-PerCP (Becton Dickinson Immunocytometry Systems Cat. #347344) for 30 minutes at 25° C. Lysing solution, (1 ml, FACS® Lysing Solution (Becton Dickinson Immunocytometry Systems Cat. No. 349202) was added and after incubation for 10 minutes at 25° C., the samples were centrifuged (10 minutes at 200× g). The pellet was resuspended in 0.5 ml phosphate buffered saline (PBS)/0.5% bovine serum albumin (BSA) and analyzed with a FACScan™ type flowcytometer using the manufacturer's directions.

Figure 2A:
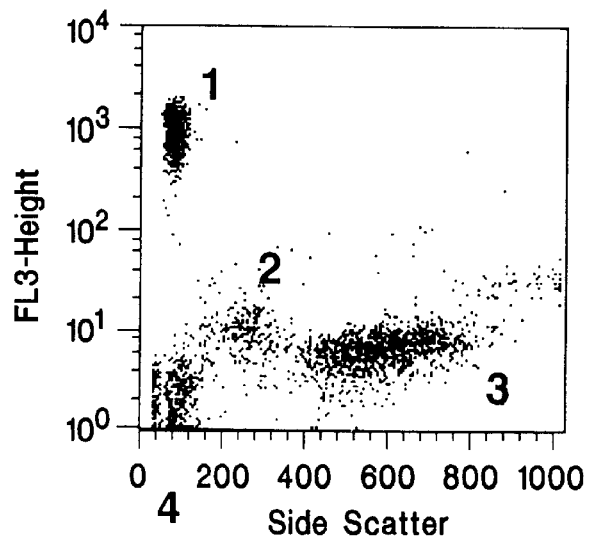
FIG. 2 compares fluorescent staining of whole blood with CD3-PerCP, the prior art CD3-PerCP-Cy5.5 (Cy5.5 "exposed"), and CD3-Cy5.5-PerCP (Cy5.5 "buried") of the invention (See Example 2). CD3 antibody labeled with Mal/Cy5.5-PerCP complex of the invention more effectively differentiates T-lymphocyte populations from other white blood cell populations with lower background than CD3 antibody labeled with Mal/PerCP-Cy5.5 of the prior art. The latter shows strong fluor-mediated binding to monocytes.
Figure 2B:
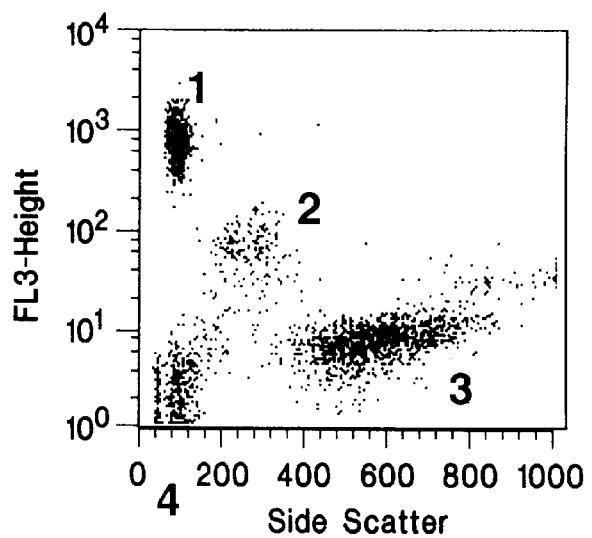
Figure 2C:
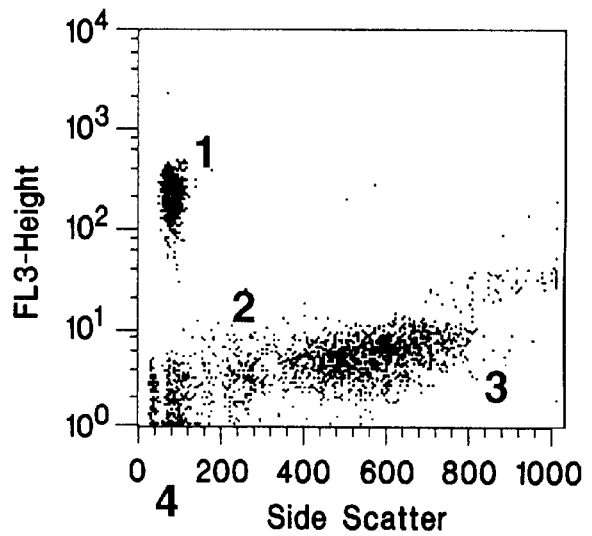

The results, shown in FIGS. 2 and 3, demonstrate the superior features of the complexes of the invention. Lymphocytes stained with CD3-Cy5.5-PerCP (Cy5.5 "buried") were approximately five times brighter than lymphocytes stained with CD3-PerCP. Importantly, fluor-specific binding of monocytes was significantly (ten-fold) lower using CD3-Cy5.5-PerCP (Cy5.5 "buried") compared with using CD3-PerCP-Cy5.5 (Cy5.5 "exposed"). In addition, the baseline gap between the monocyte peak and lymphocytes stained with CD3-Cy5.5-PerCP (Cy5.5 "buried") was significantly greater than when stained with either CD3-PerCP-Cy5.5 (Cy5.5 "exposed") or CD3-PerCP (over 1 log vs 0.1 and 0.9 logs, respectively) demonstrating that different cell populations can be more accurately assessed using the conjugates of the invention.

While the foregoing has been presented with reference to particular embodiments of the invention, it will be appreciated by those skilled in the art that changes in these embodiments may be made without departing from the principles and spirit of the invention, the scope of which is defined by the appended claims.

That which is claimed is:

1. A specific binding member labeled with an enhanced chromophore, comprising:
   a specific binding member;
   a cyanine dye having a first and a second functional group; and
   a proteinaceous fluorophore,
   wherein
   said specific binding member is coupled to said cyanine dye's first functional group,
   said proteinaceous fluorophore is coupled to said cyanine dye's second functional group, and
   said cyanine dye and said proteinaceous fluorophore are capable of fluorescence resonance energy transfer.

2. The labeled binding member of claim 1, wherein said binding member is selected from the group consisting of: antibody, antigen, hapten, nucleotides, biotin, avidin, streptavidin, ligands and receptors.

3. The labeled binding member of claim 2, wherein said binding member is an antibody.

4. The labeled binding member of claim 3, wherein said antibody is specific for CD3.

5. The labeled binding member of claim 1, wherein said cyanine dye is selected from the group consisting of Cy3, Cy3.5, Cy5, Cy5.5, Cy7 and Cy7.5.

6. The labeled binding member of claim 5, wherein said cyanine dye is a heterobifunctionalized Cy5.5.

7. The labeled binding member of claim 1, wherein said proteinaceous fluorophore is selected from the group consisting of phycobiliproteins, PE, APC, Peridinin-chlorophyll proteins (PerCP), yellow fluorescent proteins, and green fluorescent proteins.

8. The labeled binding member of claim 7, wherein said proteinaceous fluorophore is PerCP.

9. The labeled binding member of claim 6, wherein said proteinaceous fluorophore is PerCP.

10. The labeled binding member of claim 9, wherein said binding member is an antibody.

11. A method for labeling a specific binding member with an enhanced chromophore, the method comprising:
    coupling a specific binding member to a first functional group of a cyanine dye,
    wherein
    proteinaceous fluorophore has been coupled to a second functional group of said cyanine dye, and
    said cyanine dye and said proteinaceous fluorophore are capable of fluorescence resonance energy transfer.

12. The method of claim 11, further comprising the antecedent step of:
    coupling a proteinaceous fluorophore to said cyanine dye's second functional group.

13. The method of claim 11, wherein said binding member is selected from the group consisting of: antibody, antigen, hapten, nucleotides, biotin, avidin, streptavidin, ligands and receptors.

14. The method of claim 13, wherein said binding member is an antibody.

15. The method of claim 14, wherein said antibody is specific for CD3.

16. The method of claim 11, wherein said cyanine dye is selected from the group consisting of Cy3, Cy3.5, Cy5, Cy5.5, Cy7 and Cy7.5.

17. The method of claim 16, wherein said cyanine dye is a heterobifunctionalized Cy5.5.

18. The method of claim 11, wherein said proteinaceous fluorophore is selected from the group consisting of phycobiliproteins, PE, APC, Peridinin-chlorophyll proteins (PerCP), yellow fluorescent proteins, and green fluorescent proteins.

19. The method of claim 18, wherein said proteinaceous fluorophore is PerCP.

20. The method of claim 17, wherein said proteinaceous fluorophore is PerCP.

21. The method of claim 20, wherein said binding member is an antibody.

22. A method for detecting the presence in a sample of a first member of a specific binding pair, comprising:
contacting said sample with the labeled specific binding member of claim 1, wherein said labeled binding member is a second, complementary member of said specific binding pair, and then
detecting the noncovalent binding of said second member to said first member.

23. The method of claim 22, wherein said second member of said specific binding pair is selected from the group consisting of: antibody, antigen, hapten, nucleotides, biotin, avidin, streptavidin, ligands and receptors.

24. The method of claim 23, wherein said second member of said specific binding pair is an antibody.

25. The method of claim 24, wherein said antibody is specific for CD3.

26. The method of claim 22, wherein said cyanine dye is selected from the group consisting of Cy3, Cy3.5, Cy5, Cy5.5, Cy7 and Cy7.5.

27. The method of claim 26, wherein said cyanine dye is a heterobifunctionalized Cy5.5.

28. The method of claim 22, wherein said proteinaceous fluorophore is selected from the group consisting of phycobiliproteins, PE, APC, Peridinin-chlorophyll proteins (PerCP), yellow fluorescent proteins, and green fluorescent proteins.

29. The method of claim 28, wherein said proteinaceous fluorophore is PerCP.

30. The method of claim 27, wherein said proteinaceous fluorophore is PerCP.

31. The method of claim 30, wherein said second member is an antibody.

32. The method of claim 22, wherein said detecting is fluorescence detection.

33. The labeled binding member of claim 2, wherein said binding member is an antigen.

34. The labeled binding member of claim 2, wherein said binding member is a hapten.

35. The labeled binding member of claim 2, wherein said binding member is nucleotide.

36. The labeled binding member of claim 2, wherein said binding member is biotin.

37. The labeled binding member of claim 2, wherein said binding member is avidin.

38. The labeled binding member of claim 2, wherein said binding member is streptavidin.

39. The labeled binding member of claim 2, wherein said binding member is a ligand.

40. The labeled binding member of claim 2, wherein said binding member is a receptor.

41. The labeled binding member of claim 7, wherein said proteinaceous fluorophore is a phycobiliprotein.

42. The labeled binding member of claim 7, wherein said proteinaceous fluorophore is PE.

43. The labeled binding member of claim 7, wherein said proteinaceous fluorophore is APC.

44. The labeled binding member of claim 7, wherein said proteinaceous fluorophore is a yellow fluorescent protein.

45. The labeled binding member of claim 7, wherein said proteinaceous fluorophore is a green fluorescent protein.

46. The method of claim 13, wherein said binding member is an antigen.

47. The method of claim 13, wherein said binding member is a hapten.

48. The method of claim 13, wherein said binding member is nucleotide.

49. The method of claim 13, wherein said binding member is biotin.

50. The method of claim 13, wherein said binding member is avidin.

51. The method of claim 13, wherein said binding member is streptavidin.

52. The method of claim 13, wherein said binding member is a ligand.

53. The method of claim 13, wherein said binding member is a receptor.

54. The method of claim 18, wherein said proteinaceous fluorophore is a phycobiliprotein.

55. The method of claim 18, wherein said proteinaceous fluorophore is PE.

56. The method of claim 18, wherein said proteinaceous fluorophore is APC.

57. The method of claim 18, wherein said proteinaceous fluorophore is a yellow fluorescent protein.

58. The method of claim 18, wherein said proteinaceous fluorophore is a green fluorescent protein.

59. The method of claim 23, wherein said second member of said specific binding pair is an antigen.

60. The method of claim 23, wherein said second member of said specific binding pair is a hapten.

61. The method of claim 23, wherein said second member of said specific binding pair is nucleotide.

62. The method of claim 23, wherein said second member of said specific binding pair is biotin.

63. The method of claim 23, wherein said second member of said specific binding pair is avidin.

64. The method of claim 23, wherein said second member of said specific binding pair is streptavidin.

65. The method of claim 23, wherein said second member of said specific binding pair is a ligand.

66. The method of claim 23, wherein said second member of said specific binding pair is a receptor.

67. The method of claim 28, wherein said proteinaceous fluorophore is a phycobiliprotein.

68. The method of claim 28, wherein said proteinaceous fluorophore is PE.

69. The method of claim 28, wherein said proteinaceous fluorophore is APC.

70. The method of claim 28, wherein said proteinaceous fluorophore is a yellow fluorescent protein.

71. The method of claim 28, wherein said proteinaceous fluorophore is a green fluorescent protein.

* * * * *